United States Patent
Lindquist et al.

(10) Patent No.: US 6,300,538 B1
(45) Date of Patent: *Oct. 9, 2001

(54) ABSORBENT ARTICLE

(75) Inventors: Bengt W. Lindquist, Lerum; Eva Vastag, Härryda, both of (SE)

(73) Assignee: SCA Hygiene Products Aktiebolag, Goteborg (SE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/754,261

(22) Filed: Nov. 20, 1996

(30) Foreign Application Priority Data

Nov. 30, 1995 (SE) ................................... 9504277

(51) Int. Cl.⁷ ..................................................... A61F 13/15
(52) U.S. Cl. ........................ 604/369; 604/372; 604/378; 604/385.101; 604/385.24; 604/385.25; 604/385.31
(58) Field of Search ...................... 604/369, 378–382, 604/385.1, 385.2, 386, 387, 372, 385.101, 385.17, 385.24, 385.25, 385.31

(56) References Cited

U.S. PATENT DOCUMENTS

| | | | |
|---|---|---|---|
| 2,006,697 | * 7/1935 | Lindsey | 604/381 |
| 2,643,656 | * 6/1953 | Atkinson . | |
| 3,828,784 | * 8/1974 | Zoephel | 604/385.2 |
| 3,916,900 | * 11/1975 | Breyer et al. | 604/369 |
| 4,626,254 | 12/1986 | Widlund et al. . | |
| 4,666,439 | 5/1987 | Williams et al. . | |
| 4,865,597 | * 9/1989 | Mason, Jr. et al. | 604/378 |
| 5,171,302 | * 12/1992 | Buell | 604/369 |
| 5,197,959 | * 3/1993 | Buell | 604/378 |
| 5,308,346 | * 5/1994 | Sneller et al. | 604/387 |
| 5,387,210 | * 2/1995 | Murakami | 604/387 |
| 5,490,847 | * 2/1996 | Correa et al. | 604/387 |
| 5,578,025 | * 11/1996 | May | 604/385.1 |
| 5,613,961 | * 3/1997 | DiPalma et al. | 604/369 |
| 5,624,423 | * 4/1997 | Anjur et al. | 604/639 |
| 5,851,204 | * 12/1998 | Mizutani | 604/387 |

FOREIGN PATENT DOCUMENTS

| | | |
|---|---|---|
| 0 135 625 | 4/1985 | (EP) . |
| 430269 | * 6/1935 | (GB) ................................... 604/379 |
| 2281700 | * 3/1995 | (GB) . |
| WO 96/01095 | 1/1996 | (WO) . |

* cited by examiner

Primary Examiner—John G. Weiss
Assistant Examiner—K. M. Reichle
(74) Attorney, Agent, or Firm—Burns, Doane, Swecker & Mathis, L.L.P.

(57) ABSTRACT

An absorbent article (10) such as a sanitary napkin, having an elongate absorbent core (12) delimited by an upper surface (14) and a lower surface (16), a pair of opposed longitudinal edge portions (18, 20) terminating in longitudinal edges (22, 24), and a pair of opposed transverse edges (26, 28). The core has a first end portion (30), a second end portion (32) and a mid portion (34) located between the end portions. The article further includes a liquid permeable topsheet (36) extending over the upper surface (14) and a liquid impermeable sheet (38) covering the longitudinal edge portions (18, 20) of the absorbent core (12). A strip of generally hydrophobic resilient material (40) is placed between the liquid impermeable sheet (38) and the absorbent core (12) along each longitudinal edge portion (18, 20) of the absorbent core in at least the mid portion (34) to thereby increase the flexure resistance of the article.

12 Claims, 2 Drawing Sheets

ABSORBENT ARTICLE

TECHNICAL FIELD

The present invention relates to an absorbent article, such as a sanitary napkin.

BACKGROUND OF THE INVENTION

Conventional hygienic absorbent articles such as sanitary napkins, incontinence pads and the like are provided with an absorbent core which, in theory, is capable of absorbing all the fluid normally discharged by the wearer over an intended exposure time of the article. However, leakage can arise if the absorbent article is not maintained in proper relation with the wearer. One attempt to overcome this problem is to provide a sanitary napkin with so called wings. However, winged sanitary napkins also suffer from certain drawbacks. For example, if a particularly heavy discharge occurs, fluid may spread over the topsheet of the napkin and escape over the wings to thereby stain adjacent clothing. In addition, many wearers regard winged sanitary napkins as being too indiscrete.

Due to their relative narrowness, when sanitary napkins do leak this generally occurs at the side edges. Many attempts have been made to overcome the problem of edge leakage, including that described in U.S. Pat. No. 4,666,439. In said document, a sanitary napkin is disclosed which comprises an elongate absorbent core having a liquid pervious sheet over its front face and a liquid impervious barrier sheet over its back face. The liquid impervious barrier sheet has edge portions which cover the longitudinal sides and the side margins at the front face of the absorbent core. In an effort to inhibit leakage of body fluids from the front surface of the absorbent pad to the sides thereof, said document teaches providing a layer of water absorbing polymer in contact with a surface of the barrier sheet in the longitudinal edge portions.

Whilst the sanitary napkin according to said U.S. Pat. No. 4,666,439 may exhibit improved side edge leakage protection when compared to a conventional sanitary napkin, a need still exists for a sanitary which reduces further the risk of side edge leakage whilst still being sufficiently discrete to satisfy the majority of wearers. It is therefore an object of the present invention to provide an absorbent article which meets these requirements.

SUMMARY OF THE INVENTION

The above-stated object is achieved in accordance with the present invention by an absorbent article comprising:

- an elongate absorbent core delimited by an upper surface and a lower surface, a pair of opposed longitudinal edge portions terminating in longitudinal edges, and a pair of opposed transverse edges, said core having a first end portion, a second end portion and a mid portion located between said end portions;
- a liquid permeable topsheet extending over said upper surface, and
- a liquid impermeable sheet covering said longitudinal edge portions of said absorbent core, wherein a strip of substantially hydrophobic resilient material is arranged between said liquid impermeable sheet and said absorbent core along each longitudinal edge portion of said absorbent core in at least said mid portion of said absorbent core to thereby increase the flexure resistance of the article.

The provision of strips of resilient material in at least the mid portion of the absorbent article according to the invention increases the shape stability of the article in the strike zone, i.e. that region of the absorbent article which is first contacted by discharged bodily fluid. In this manner, the risk of bunching of the absorbent article is significantly reduced. In addition, the resilient strips press the longitudinal edges of the absorbent article towards the wearer, thereby causing the article to more readily mould to the body of the wearer. Since the strips need not extend along the entire length of the article, the article may be worn discretely. Advantageously, the remote ends of the strips may serve to impart a bowl-shape to the article to further conform the article to the shape of the wearer.

BRIEF DESCRIPTION OF THE DRAWINGS

The invention will be described in the following by way of example only and with reference to the attached drawings, in which.

DETAILED DESCRIPTION OF PREFERRED EMBODIMENTS

Figure 1:
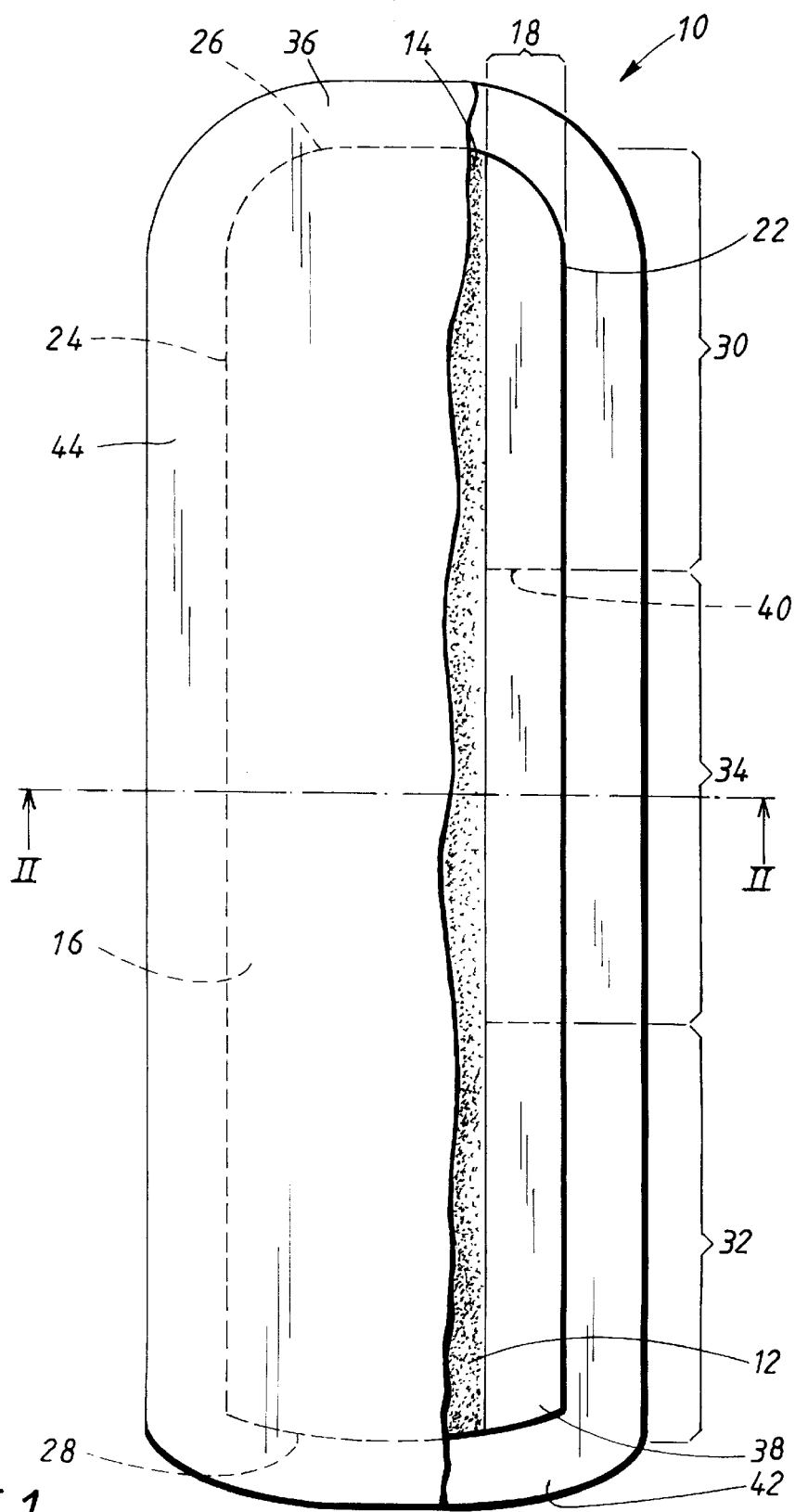
FIG. 1 is a schematic plan view of an absorbent article according to the present invention with a partially cut away topsheet.

In the drawings, reference numeral 10 generally denotes an absorbent article according to the invention. As is apparent from FIG. 1, the absorbent article 10 may be a sanitary napkin having an elongate absorbent core 12 delimited by an upper surface 14 and a lower surface 16. The core 12 may be any conventional absorbent core, though a preferred core is of the type disclosed in GB-A-2,281,700. The absorbent core further includes opposed longitudinal edge portions 18, 20 terminating in longitudinal edges 22, 24, and a pair of opposed transverse edges 26, 28. The core is made up of a first end portion 30, a second end portion 32 and a mid portion 34 located between the end portions. The sanitary napkin is intended to be placed relative the wearer in use so that the strike zone lies within the mid portion 34.

As is typical in the art, the absorbent article 10 is further provided with a liquid permeable topsheet 36 extending over the upper surface 14 of the absorbent core 12. The topsheet 36 may be any conventional topsheet. For example, it may be made from a multi-apertured plastics film of the type disclosed in U.S. Pat. No. 4,626,254, or a nonwoven material.

The sanitary napkin 10 as illustrated by way of example in the drawings further comprises a pair of liquid impermeable sheets 38, with each sheet covering a longitudinal edge portion 18, 20 of the absorbent core. The liquid impermeable sheets are preferably coated with adhesive on their concave surface, i.e. the surface facing towards the absorbent body. Although a pair of sheets has been shown in the drawings, it is to be realized, however, that the two sheets 38 may be replaced by a single sheet extending over the entire lower surface 16 of the absorbent core.

Figure 2:
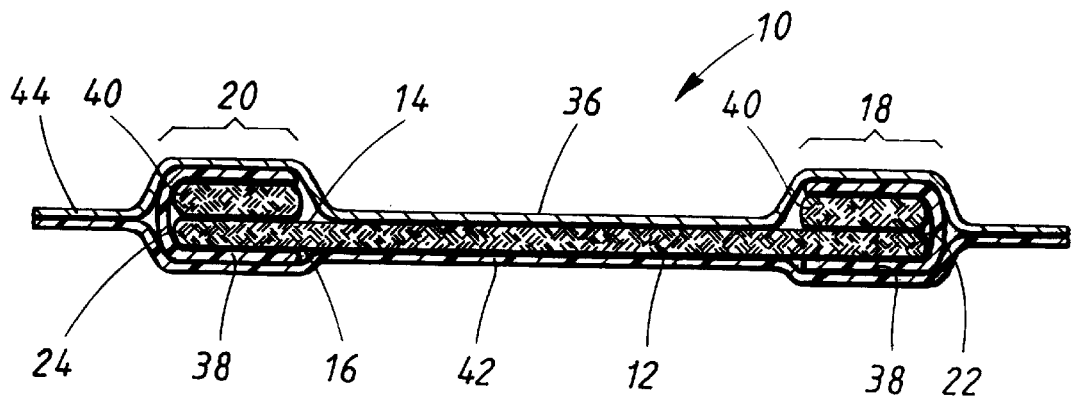
FIG. 2 is a sectional view on a larger scale along line II—II of FIG. 1.

In accordance with the present invention, and as best illustrated in FIG. 2, a strip of resilient material 40 is placed between each liquid impermeable sheet 38 and the absorbent core 12 along each longitudinal edge portion 18, 20 of the absorbent core in at least the mid portion 34 of the absorbent core. The strips of resilient material serve i.e., to significantly increase the stiffness of the sanitary napkin in the region of the mid portion. In other words, the resistance to flexure in the longitudinal direction is increased by at least 10% in the longitudinal edge portions in the mid portion when compared to a sanitary napkin without strips of resilient material.

The strips of resilient material 40 are primarily hydrophobic and may be a three dimensional nonwoven fibrous plastic wadding or a foamed plastic. Since the material of the strips is primarily hydrophobic, migrating body fluids tend to flow through the absorbent core rather than through the strips of resilient material. Since, in the embodiment shown in FIG. 2, the strips of resilient material serve to conceal the longitudinal edge portions 18, 20 in the mid portion 34, any collection of fluid at the edge portions is concealed, thereby imparting an impression of increased safety to the wearer.

Figure 3:
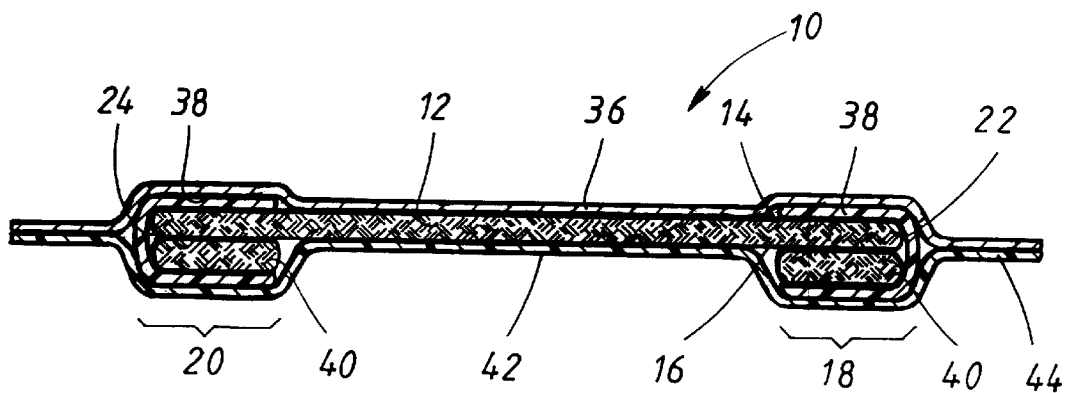
FIG. 3 is a sectional view through a second embodiment of the invention.

In a further embodiment of the invention, and as illustrated in FIG. 3, strips of resilient material 40 are placed between the liquid impermeable sheets 38 and the lower surface 16 of the absorbent core 12. Preferably, however, the strips of resilient material are placed between the liquid impermeable sheets 38 and the upper surface 14 of the absorbent core, as shown in FIG. 2. In this manner, the strips of resilient material 40 serve to "lift" the liquid impermeable sheets 38 from the upper surface 14 of the absorbent core to thereby create an opening to a liquid-retaining pocket formed by the liquid impermeable sheet along each longitudinal edge portion 18, 20. Accordingly, any discharged bodily fluids which migrate across the upper surface of the absorbent core will flow through the opening and into the liquid-retaining pocket. Due to the fact that the concave surfaces of the sheets of resilient material are coated with adhesive and thereby adhere to the absorbent core and strips of resilient material, the risk of fluids leaking from the liquid-retaining pockets is minimal.

Particularly in the case when the absorbent article according to the invention comprises a pair of liquid impermeable sheets 38 covering the longitudinal edge portions 18, 20 of the absorbent core 12, the absorbent article may also comprise a liquid impermeable backsheet 42 extending over the lower surface 16 of the absorbent core. Advantageously, the backsheet 42 is made of the same material as the liquid impermeable sheet 38 and is joined to the topsheet 36 to form a peripheral margin 44 around preferably the entire absorbent core 12. In this manner, the liquid-retaining pockets along the edge portions 18, 20 are enclosed by the topsheet 36 and the backsheet 42.

For ease of manufacturing and to ensure that the risk of edge leakage anywhere along the length of the absorbent article is minimal, the liquid-retaining pockets preferably extend along the entire length of the absorbent core. Since, however, the form stability of the absorbent article is most critical only in the mid portion 34 of the absorbent core, the strips of resilient material 40 need only occupy said mid portion. However, if desired, the strips may extend into the first and second end portions 30, 32.

Advantageously, the mid portion 34 of the absorbent core 12 comprises between 20% and 60%, preferably between 30 and 45%, and most preferably about one third, of the length of the absorbent core.

Obviously, the hydrophobic strips of resilient material 40 may not extend over the entire width of the absorbent core since this would prevent passage of body fluids into the absorbent core 12. Accordingly, each strip of resilient material 40 has an extension transversely across the absorbent core, with the extension being between 5% and 25% of the total width of the absorbent core. The liquid impermeable sheets 38 advantageously display the same or similar transverse extension as the strips of resilient material. The thickness of the strips of resilient material 40, i.e. the extension of the strips in a direction substantially perpendicular to the upper surface of the absorbent core, should be sufficient to allow the strips to mould to the wearer's body. Typically, the thickness of the strips in an uncompressed condition can thus lie between about 1 and 5 mm.

The absorbent article 10 described above and shown in the drawings may be manufactured using the following process.

Two lengths of liquid impermeable sheet are cut from a roll of backsheet material and coated on one side with an adhesive. Discrete strips of resilient material are then placed intermittently along the lengths of liquid impermeable material. The lengths of material are then fed into a binding machine so that the strips of resilient material are positioned in the mid portion of the absorbent cores. The lengths of material are then folded over the longitudinal edges of the absorbent cores and the products separated. The topsheet and backsheet are thereafter applied in a conventional manner.

The invention is not restricted to the embodiments described above and shown in the drawings, but may be modified within the scope of the appended claims. For example, strips of resilient material may be placed on both surfaces of the absorbent core in the longitudinal edge portions.

What is claimed is:

1. An absorbent article, comprising:
    an elongate absorbent core delimited by an upper surface and a lower surface, a pair of opposed longitudinal edge portions terminating in longitudinal edges, and a pair of opposed transverse edges, said core having a first end portion, a second end portion and a mid portion located between said end portions;
    a liquid permeable topsheet extending over said upper surface, and
    a pair of liquid impermeable sheet, each of the liquid impermeable sheets covering a respective one of said longitudinal edge portions of said absorbent core to form a liquid retaining pocket along the respective one of said longitudinal edge portions, wherein a strip of substantially hydrophobic resilient material is arranged between each of said respective liquid impermeable sheets and said absorbent core along each longitudinal edge portion of said absorbent core in at least said mid portion of said absorbent core to thereby increase the flexure resistance of the article;
    wherein each of the liquid impermeable sheets covers a portion of the upper surface of the absorbent core, a portion of the lower surface of the absorbent core, and at least a portion of the longitudinal edge of the respective longitudinal edge portion of the absorbent core.

2. The absorbent article as claimed in claim 1, wherein each of the strips of hydrophobic material is a three dimensional nonwoven fibrous plastic wadding.

3. The absorbent article as claimed in claim 1, wherein each of the strips of hydrophobic material is foamed plastic.

4. The absorbent article as claimed in claim 1, wherein each of the strips of resilient material is arranged between a respective one of said liquid impermeable sheets and said upper surface of said absorbent core.

5. The absorbent article as claimed in claim 1, wherein each of the strips of resilient material is arranged between a respective one of said liquid impermeable sheets and said lower surface of said absorbent core.

6. The absorbent article as claimed in claim 1, wherein the absorbent article further comprises a liquid impermeable backsheet extending over said lower surface of said absorbent core, said backsheet and said topsheet being joined to form a peripheral margin around said absorbent core.

7. The absorbent article as claimed in claim 6, wherein said pockets extend along an entire length of said absorbent core.

8. The absorbent article as claimed in claim 1, wherein said mid portion of said absorbent core comprises between 20% and 60% of a length of the absorbent core.

9. The absorbent article as claimed in claim 1, wherein each of said strips of resilient material has an extension transversely across said absorbent core, said extension being between 5% and 25% of the total width of the absorbent core.

10. The absorbent article as claimed in claim 1, wherein said mid portion of said absorbent core comprises between 30 and 45% of the absorbent core.

11. The absorbent article as claimed in claim 1, wherein said mid portion of said absorbent core comprises about one-third of a length of the absorbent core.

12. The absorbent article as claimed in claim 1, wherein each of the liquid impermeable sheets forms a C-fold around an exterior periphery of the respective longitudinal edge portion.

* * * * *